US010459624B2

(12) United States Patent
Wellhöfer et al.

(10) Patent No.: US 10,459,624 B2
(45) Date of Patent: Oct. 29, 2019

(54) APPARATUS EQUIPPED WITH A TOUCHSCREEN AND METHOD FOR CONTROLLING SUCH AN APPARATUS

(71) Applicant: Wavelight GmbH, Erlangen (DE)

(72) Inventors: Armin Wellhöfer, Schwaig (DE); Tobias Jeglorz, Stein (DE)

(73) Assignee: Wavelight GmbH

( * ) Notice: Subject to any disclaimer, the term of this patent is extended or adjusted under 35 U.S.C. 154(b) by 677 days.

(21) Appl. No.: 14/837,776

(22) Filed: Aug. 27, 2015

(65) Prior Publication Data

US 2016/0092099 A1     Mar. 31, 2016

(30) Foreign Application Priority Data

Sep. 25, 2014   (DE) .................. 10 2014 014 498

(51) Int. Cl.
*G06F 3/0488*     (2013.01)
*G06F 3/0481*     (2013.01)
(Continued)

(52) U.S. Cl.
CPC .......... *G06F 3/04883* (2013.01); *G06F 3/016* (2013.01); *G06F 3/0416* (2013.01)

(58) Field of Classification Search
CPC ...... G06F 3/016; G06F 3/0416; G06F 3/0481; G06F 3/0484; G06F 3/0488; G06F 3/04883; G06F 2203/04808; A61B 3/0033
(Continued)

(56) References Cited

U.S. PATENT DOCUMENTS

2006/0026532 A1    2/2006  Pagan
2006/0053387 A1*   3/2006  Ording ............... G06F 3/04883
                                                                      715/773
(Continued)

FOREIGN PATENT DOCUMENTS

DE    112007001143 T5    4/2009
EP        2634684 A2     9/2013
(Continued)

OTHER PUBLICATIONS

Google; "Galaxy Nexus User Guide"; Jan. 1, 2012; XP055214629; Retrieved from the Internet: URL:http://nexusmanual.com/wp-content/uploads/2012/09/Google-Sumsung-Nexus-Galaxy-Manual-For-Android-4-Jerry-Bean.pdf [retrieved on Sep. 18, 2015] slide 12.

*Primary Examiner* — Matthew Ell
*Assistant Examiner* — Maria S Ayad
(74) *Attorney, Agent, or Firm* — Keiko Ichiye, Esq.

(57) ABSTRACT

In one embodiment, an apparatus comprises a touchscreen and a control device for executing an operating command which is input on the user side via the touchscreen. The control device is adapted to control the touchscreen such that, in order to prompt a command input, a first graphic element marking a touching starting location and a destination graphic arrangement having at least one second graphic element at a distance from the first graphic element are displayed on the touchscreen. The control device is further adapted to recognise a command input depending detecting a first movement of at least one object over the touchscreen starting from the touching starting location continuously up to a second graphic element of the destination graphic arrangement and on reaching this second graphic element a movement stoppage of the object, followed by a follow-up action of the object on the touchscreen.

29 Claims, 5 Drawing Sheets

(51) Int. Cl.
*G06F 3/0484* (2013.01)
*G06F 3/01* (2006.01)
*G06F 3/041* (2006.01)

(58) Field of Classification Search
USPC .......................................................... 715/863
See application file for complete search history.

(56) References Cited

U.S. PATENT DOCUMENTS

| | | | |
|---|---|---|---|
| 2006/0112335 A1 | 5/2006 | Hofmeister et al. | |
| 2007/0150834 A1 | 6/2007 | Muller et al. | |
| 2009/0073117 A1* | 3/2009 | Tsurumi | G06F 3/005 345/158 |
| 2009/0109187 A1* | 4/2009 | Noma | G06F 3/04883 345/173 |
| 2010/0231550 A1* | 9/2010 | Cruz-Hernandez | G06F 3/016 345/174 |
| 2010/0251154 A1 | 9/2010 | Chang et al. | |
| 2011/0060986 A1* | 3/2011 | Yang | G06F 3/04845 715/702 |
| 2012/0081303 A1* | 4/2012 | Cassar | G06F 1/1616 345/173 |
| 2012/0252410 A1 | 10/2012 | Williams | |
| 2012/0311509 A1* | 12/2012 | Maggiotto | G06F 3/04817 715/863 |
| 2012/0327122 A1* | 12/2012 | Imamura | G06F 3/04815 345/649 |
| 2013/0145307 A1 | 1/2013 | Kawasaki | |
| 2013/0227490 A1* | 8/2013 | Thorsander | G06F 3/0482 715/841 |
| 2013/0285925 A1* | 10/2013 | Stokes | G06F 3/04883 345/173 |
| 2013/0328786 A1* | 12/2013 | Hinckley | G06F 3/033 345/173 |
| 2014/0033040 A1* | 1/2014 | Thomas | G06F 3/0488 715/721 |
| 2014/0096052 A1 | 4/2014 | Aoshima et al. | |
| 2014/0108989 A1* | 4/2014 | Bi | G06F 3/04886 715/773 |
| 2014/0165006 A1 | 6/2014 | Chaudhri et al. | |
| 2015/0070283 A1* | 3/2015 | Irwin | G06F 3/0416 345/173 |
| 2015/0169151 A1* | 6/2015 | Urakawa | G06F 3/0485 715/776 |
| 2015/0277743 A1* | 10/2015 | Isherwood | G06F 1/1626 715/863 |

FOREIGN PATENT DOCUMENTS

| | | |
|---|---|---|
| JP | 6124167 A2 | 5/1994 |
| JP | 2012133787 A2 | 7/2012 |
| JP | 2013-025357 A | 2/2013 |
| JP | 2014-021936 A | 2/2014 |

\* cited by examiner

APPARATUS EQUIPPED WITH A TOUCHSCREEN AND METHOD FOR CONTROLLING SUCH AN APPARATUS

TECHNICAL FIELD

The present disclosure relates to apparatuses equipped with a touchscreen and a method for controlling such an apparatus.

BACKGROUND

In computer-based apparatuses, touchscreens are being increasingly employed to detect operating commands. What is referred to as a touchscreen is a display device which is adapted, on the one hand, to display pictorial information and, on the other hand, detect position(s) of one or more objects interacting with the touchscreen, for example touching the touchscreen. With the touchscreen, the user can immediately select an object displayed on the touchscreen without the aid of conventional input means, such as computer keyboards, joysticks or computer mice. The operation of the computer-based apparatus is thereby facilitated. Moreover, touchscreens usually feature easily cleaned outer surfaces, which is why they are preferred over conventional input means.

In order to input an operating command, the user may touch a touch-sensitive surface of the touchscreen at a place at which a graphic element representing the operating command is displayed. The graphic element may be, for example, a wastepaper basket or a control button with a textual explanation representing the command, e.g., "Laser ON" (i.e. switch on the laser). If, for example, the wastepaper basket is selected, i.e. the user touches the touchscreen in the region of the wastepaper basket, previously selected data or files may be deleted, and if the control button, "Laser ON" is selected, a laser may be put into an operating state in which a laser beam is emitted.

Commands of this type may have irreversible consequences, since deleted data or, in the above example, tissue treated by the laser beam cannot be readily restored. In order to avoid operating errors in the case of irreversible or safety-critical commands, a hurdle to operating errors may be provided whereby a command input has to be confirmed by an additional input. To this end, for example, a safety query may be displayed on the display of the touchscreen, enabling the user to confirm or cancel the operating command.

By way of example, reference is made in this regard to known art, e.g., by Microsoft applications, where an input window displayed on a graphical user interface of a touchscreen can be seen, by means of which the user may be prompted, for example by a program executed on the computer-based apparatus, to confirm a command proposed by the apparatus. One in the art is familiar with a question like "Delete all measurement data?", which may be displayed on the touchscreen. In order to answer this question, the user may have the option to confirm the proposed command by selecting an "OK", "Yes" or equivalent control button (equivalent in the sense of a semantic relationship to "OK" or "Yes") or reject it by selecting a "Cancel", "No" or equivalent control button. After selection of the control button, however, the associated operation (e.g., deletion operation) may not be carried out directly. Instead, the user may be prompted with a safety question to confirm the operation; for example, a query field "Delete all measurement data. Are you sure?" may be displayed. Only after the user has answered the safety question by selecting/activating an associated control box displayed on the touchscreen, is the measurement data deleted in accordance with the command.

This kind of confirmation of an operating command is comparatively cumbersome and the duration of the entire command input is relatively long.

Against this background, it is an object of the present invention to provide an apparatus and a method for controlling such an apparatus which are distinguished by a user-friendly and at the same time safe operation.

SUMMARY OF EXAMPLE EMBODIMENTS

According to a first aspect, in this regard, a method for controlling an apparatus equipped with a touchscreen is provided, wherein the method comprises the execution of an operating command which is input on the user side via the touchscreen, wherein, in order to prompt a command input, a first graphic element marking a touching starting location and a destination graphic arrangement having at least one second graphic element at a distance from the first graphic element are displayed on the touchscreen, wherein a command input is recognised depending on there being detected a first movement of at least one object over the touchscreen starting from the touching starting location continuously up to a second graphic element of the destination graphic arrangement, and on reaching this second graphic element a movement stoppage of the object, followed by a follow-up action of the object on the touchscreen.

The graphic elements (first graphic element, second graphic element) can contain, for example, textual elements or/and pictorial elements or/and symbolic elements. The touching starting location marked by the first graphic element can be of punctual nature or the first graphic element can provide an areal region, within which the user can touch any desired place or any desired partial region and use it as a touching starting location.

The follow-up action can comprise a stationary dwelling of the object at the second graphic element reached for a preset minimum duration. This minimum duration can lie, for example, in the range between 0.3 and 2.0 seconds. Alternatively or additionally, the follow-up action can comprise a follow-up movement of the object over the touchscreen starting from the second graphic element reached in the direction away from the latter. The follow-up movement here has advantageously to take place in a direction transversely with respect to the direction of the first movement, for instance in the manner of a hooked movement.

In specific embodiments, the command input is recognised depending on the follow-up action being detected without intermediate lifting-off of the object from the touchscreen after the first movement. In other embodiments, by contrast, intermediate lifting-off of the object from the touchscreen after the first movement is required or at least not a hindrance before the follow-up action is performed. Thus, in specific embodiments, the follow-up action can comprise, for example, a renewed movement of the object over the touchscreen starting from the touching starting location continuously up to the second graphic element reached on the first movement. In other words, in these embodiments, the first movement is to be performed once again substantially according to the same movement pattern, so to speak as a confirmation of the first movement. In other embodiments, the follow-up action can comprise a renewed touching by means of the object of the second graphic element reached after intermediate lifting-off of the object from the touchscreen. In such embodiments, the command input can be concluded by the user, after he or she has completed the first movement with the object, tapping the second graphic element reached with the object once again for confirmation purposes.

Irrespective of whether intermediate lifting-off of the object from the touchscreen between the first movement and the follow-up action is required or undesirable, there can be displayed on the touchscreen an optical indication which disappears depending on the follow-up action being performed. The optical indication serves, so to speak, as a reminder for the user that he or she has still to perform the follow-up action and must not forget it. For example, the optical indication can comprise a flashing of a graphic element displayed on the touchscreen, for instance a flashing of the first graphic element or of the second graphic element reached on the first movement. Other visualisation means which can be understood by a user as an indication of the necessity for the still outstanding follow-up action are readily conceivable. For example, a visually perceptible indicating effect can be achieved via the colour, the colour saturation, the degree of transparency or/and the display size of the first graphic element or/and of the second graphic element.

According to specific embodiments, on detection of the first movement, the first graphic element is displaced on the touchscreen in the direction towards the second graphic element preferably synchronously with the moving object. This concomitant movement of the first graphic element with the moving object supplies the user with a visual acknowledgement about the effectiveness of his or her operating activities on the touchscreen. Here, the displaced first graphic element can be locked at the second graphic element, for example, in at least partial superimposition of the latter, depending on the follow-up action also being detected. If the follow-up action has not yet begun or at least is not yet concluded, the displaced first graphic element can jump back after lifting-off of the object from the touchscreen to the original position where it was located at the beginning of the first movement. Such a jumping-back of the first graphic element signals to the user that the command input is not yet concluded and that he or she has to perform, for this purpose, a renewed movement of the object on the touchscreen from the touching starting location up to the desired second graphic element.

In specific embodiments, the destination graphic arrangement can have a plurality of at least two second graphic elements which are arranged at a distance from one another and each of which is assigned a different operating command. In such a configuration, the first graphic element can be displayed, for example, at a place on the touchscreen where it is centred with respect to the second graphic elements of the destination graphic arrangement. Other arrangement patterns of the first graphic element relative to the second graphic elements are, of course, possible.

According to further embodiments, one of the second graphic elements can signify a confirmation of a called apparatus function, for example, of a function for storing or deleting or modifying data, and another of the second graphic elements can signify a rejection of this apparatus function.

In other embodiments, the operating command causes an adjustment of an adjustable component of the apparatus into one of a plurality of different predefined adjustment states, e.g., positions. The adjustable component can be, for example, a patient chair, a patient couch, a slit lamp or a laser head. Each of the adjustment states here is assigned a different second graphic element.

In specific embodiments, a haptic and/or visual and/or acoustic acknowledgement is output by the apparatus after at least part of the follow-up action. This acknowledgement can serve as confirmation of a successful input of the operating command for the user.

In correspondence with the first method aspect, there is provided an apparatus, having a touchscreen and a control device, coupled to the touchscreen, for executing an operating command which is input on the user side via the touchscreen. The control device is adapted to control the touchscreen in such a manner that, in order to prompt a command input, a first graphic element marking a touching starting location and a destination graphic arrangement having at least one second graphic element at a distance from the first graphic element are displayed on the touchscreen. The control device is further adapted to recognise a command input depending on there being detected a first movement of at least one object over the touchscreen starting from the touching starting location continuously up to a second graphic element of the destination graphic arrangement and on reaching this second graphic element a movement stoppage of the object, followed by a follow-up action of the object on the touchscreen.

A second method aspect of the present disclosure provides a method for operating an apparatus equipped with a touchscreen, wherein, in the method, in response to a predefined operating command, a view on the touchscreen changes from a first menu page to a second menu page.

An input of the operating command is recognised depending on a first movement of an object over the touchscreen being detected and simultaneously or at least partly temporally overlapping with respect thereto at least one further movement of an object over the touchscreen along a movement path which is different from a movement path of the first movement being detected, or/and a stationary dwelling of an object on the touchscreen at a place distant from the movement path of the first movement being detected. Such a movement can be, for example, a swiping movement or a dragging movement. With such a coupling of a first movement to at least one further movement or/and a stationary dwelling of an object on the touchscreen as a condition for the successful input of an operating command, increased safety with respect to an unintended operating error and thus an unintended activation of specific apparatus functions can be afforded. Such operating errors may occur not only in the context of the control of the apparatus by operating control fields on the touchscreen within one and the same menu view, but also in the navigation through different menu pages of an operating menu. Navigation errors within the often highly branched tree of menu pages which an operating menu of an apparatus may have, easily lead to delays in the treatment process or even to the activation of incorrect apparatus functions. The solution according to the second method aspect can ensure that the change from one screen view to another is not activated unintentionally by, for example, an uncontrolled movement or gesture not intended at all by the user as a specific command, for example, in the form of a swinging movement of a hand or the presenting or pointing with a hand or a device provided therefor.

In embodiments it can be provided that an input of the operating command is recognised depending on the movement paths of the first and each further swiping movement running without intersecting one another and if desired running longitudinally beside one another.

The number of parallel movements (parallel here in the sense of simultaneous or at least partly temporally overlapping) can be specified in the second method aspect, for example, depending on the capabilities of the touchscreen. Modern touchscreens can detect more than two fingers (or devices, such as pens or other objects) which are placed simultaneously on the touchscreen. Some touchscreens, for example, can detect up to ten fingers. Accordingly, with such touchscreens, it can be provided that a successful input of a command for changing menu pages requires the temporally parallel detection of a swiping gesture of up to ten fingers (or generally: objects) on the touchscreen. However, embodiments are, of course, also possible in which the first movement and only a single further movement are sufficient to be able to input the operating command successfully.

It can be provided that specific criteria are specified beforehand for the relative position and/or orientation of the movement paths of the objects on the touchscreen, which criteria are to be observed in order to be able to input a command for changing menu pages successfully. For example, it can be specified that a movement path must be within a given tolerance band in relation to a neighbouring movement path, in order to be able to be a basis for the successful command input. If the movement path leaves the tolerance band, the command input fails or the relevant movement is rejected as invalid. Alternatively or additionally, a predetermined position or/and orientation relative to the touchscreen can be specified for the movement paths. For example, it can be provided that all movement paths must lie only within a specific, e.g., central horizontal, strip on the touchscreen, in order to be able to serve as a basis for a successful command input. Alternatively or additionally, specific requirements may be placed on the movement paths as regards the path length or/and the duration of the individual movements.

In specific embodiments, it can be provided that an input of the operating command is recognised depending on paired neighbouring movement paths observing, at least on part of their path length, a predefined minimum spacing and/or a predefined maximum spacing. Alternatively or additionally, it can be provided that an input of the operating command is recognised depending on paired neighbouring movement paths—insofar as they do not already run at a uniform spacing from one another anyway—run at an angle to one another which does not exceed a predetermined maximum angle, for example a maximum angle of 5 degrees.

In some embodiments, an input of the operating command is recognised depending on the stationary dwelling of an object at a place within a predefined region of the touchscreen being detected. This predefined region can be, for example, a corner region of the touchscreen.

For the duration of the stationary dwelling of an object on the touchscreen, a minimum value can be specified beforehand, for example 0.5 or 1.0 or 1.5 or 2.0 seconds. For a successful input of an operating command, there can additionally be a prerequisite that the stationary dwelling of an object satisfies a predefined time relationship with respect to the first movement. This time relationship may, for example, relate to the beginning of the stationary dwelling or/and its duration or/and its end. Numerous constellations can be envisaged here. To give an example which is in no way limiting, it could be provided that the beginning of the stationary dwelling must lie before the beginning of the first movement, and that the user must maintain the stationary dwelling continuously until after the end of the first movement.

In correspondence with the second method aspect, the present disclosure also provides an apparatus having a touchscreen and a control device coupled to the touchscreen, wherein the control device is adapted to control the touchscreen in such a manner that, in response to a predefined operating command, a view on the touchscreen changes from a first menu page to a second menu page. The control device is adapted to recognise an input of the operating command depending on a first movement of an object over the touchscreen being detected and simultaneously or at least partly temporally overlapping with respect thereto at least one further swiping movement of an object over the touchscreen along a movement path which is different from the movement path of the first movement being detected, or/and a stationary dwelling of an object on the touchscreen at a place distant from the movement path of the first movement being detected.

BRIEF DESCRIPTION OF FIGURES

The invention will be further explained below with the aid of the appended drawings, taking a medical apparatus, in particular an ophthalmological apparatus, as an example. In the drawings.

DETAILED DESCRIPTION OF EXAMPLE EMBODIMENTS

The ophthalmological apparatuses considered by way of example in the context of the present disclosure can serve for operative purposes or/and diagnostic purposes, i.e. include suitable devices for therapeutic or/and surgical treatment or/and diagnostic investigation of a human eye.

In specific embodiments the ophthalmological apparatus is or comprises a laser apparatus which provides focused laser radiation having suitable radiation parameters for laser treatment of human eye tissue, and which is equipped with a suitable control for moving the laser radiation and especially its focus in space and time to achieve the desired treatment result. The laser treatment can comprise, for example, making cuts in the cornea or in the region of the human lens or in other parts of the eye tissue by lining up a large number of damage zones caused by the effect of photodisruption and locally limited approximately to the focus dimensions of the laser radiation. The laser radiation used for this is short-pulsed with a pulse duration in the range of femto-, pico-, nano- or even atto-seconds and has a wavelength which ensures a transmission of the radiation into the eye tissue, for example, a wavelength in the UV range above about 300 nm or in the IR range between about 800 nm and 1900 nm. Alternatively or additionally, the laser treatment can comprise, for example, a photoablative removal of a tissue volume from the surface of a tissue part of the eye (e.g., the cornea) by means of laser radiation with a wavelength at which a transmission does not take place through the irradiated tissue (typically below 300 nm). For example, an Argon Flouride (ArF) excimer laser emitting at about 193 nm can be used for such photoablative treatment.

Figure 1:
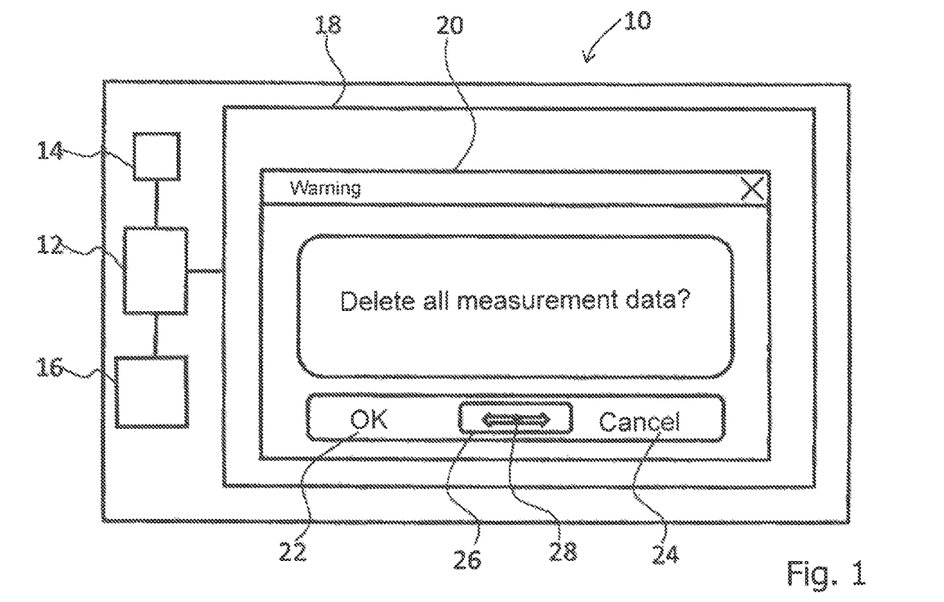
FIGS. 1 and 2 show a first embodiment for inputting an operating command in an ophthalmological apparatus via a touchscreen.
Figure 2:
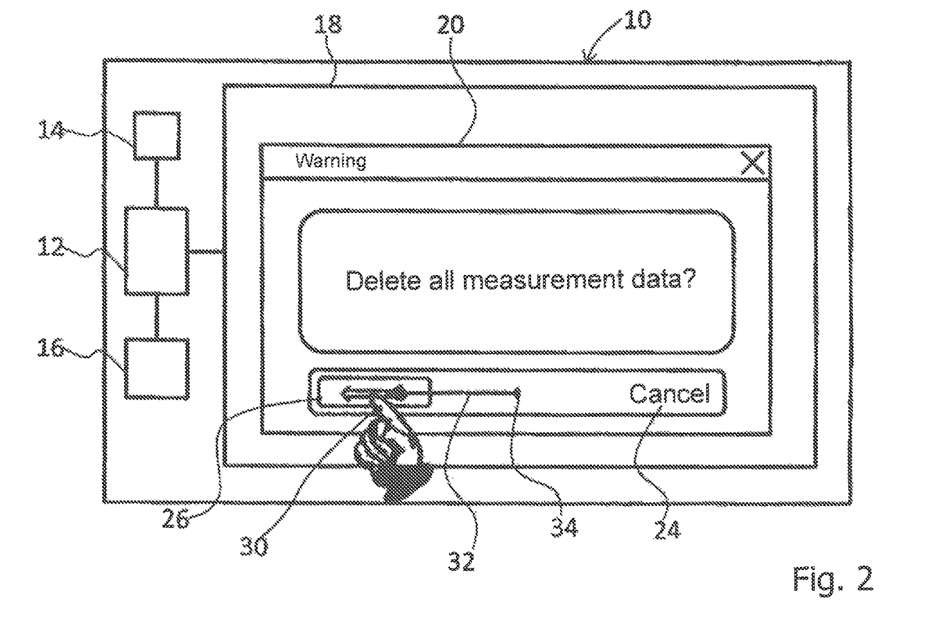

Reference is made first of all to the first embodiment according to FIGS. 1 and 2. There, a rectangular box 10 is used to indicate highly schematically an apparatus which can be found in an ophthalmologist's practice or an eye clinic for ophthalmological purposes. The ophthalmological apparatus 10 can serve, for example, for the laser treatment of human eye tissue and can be equipped with a laser source (not shown specifically) which provides laser radiation having radiation parameters suitable for the intended laser treatment. Alternatively or additionally, the ophthalmological apparatus 10 can enable diagnostic investigations of a human eye, for example determination of the topography of the surface of the eye (e.g., the front surface of the cornea), determination of a thickness profile of a cornea by means of pachymetric methods, taking of two- or three-dimensional pictures of the eye or parts thereof by means of Optical Coherence Tomography (OCT) methods, carrying out of wavefront measurements on the eye and the like. The list of these exemplary diagnostic investigations is in no way limiting; the technical means required for carrying out such diagnostic investigations, as well as those for carrying out laser treatment, of the human eye are known per se in the art and therefore do not require further explanation here.

In the first embodiment according to FIGS. 1 and 2, the ophthalmological apparatus 10 has an electronic, program-controlled control device 12 which is connected to a memory 14, in which measurement data (and if desired other data) are stored. To obtain the measurement data, the ophthalmological apparatus 10 comprises a measuring device 16, the concrete form of which is of no further importance here. It suffices to note that the measuring device 16 delivers measurement data which is stored in the memory 14 and obtained, for example, by measurements on a patient's eye.

The ophthalmological apparatus 10 furthermore has a touchscreen 18, which is a display device, the display area of which (or at least part of the same) is of touch-sensitive design, i.e. responds to touches by an object approaching the display area and generates corresponding electrical signals and delivers them to the control device 12. From the touch signals delivered by the touchscreen 18, the control device 12 determines whether specific touch patterns are present which can be interpreted as valid input of an operating command. The technology of such touchscreens is known per se; further explanation is therefore unnecessary here. It should be emphasised, however, that in the context of the present disclosure, both capacitive and pressure-sensitive touchscreens are possible, so that the term touching here is not to be understood as necessarily presupposing actual contact, as in the case of pressure-sensitive touchscreens. In the case of capacitively acting touchscreens, a "touching" can already be detected even before an approaching object has actually been placed on the touchscreen.

The object used to operate the touchscreen 18 can be, for example, at least one finger of at least one hand. Alternatively, pen-shaped pointing instruments can be used. The representation of a human hand shown in some of the figures is thus to be understood merely as an example.

To explain a first procedure for inputting an operating command via the touchscreen 18, a dialog field 20 can be seen in FIGS. 1 and 2, which field is displayed on the display area of the touchscreen 18 and asks the user whether he or she would like to delete existing measurement data ("Delete all measurement data?"). The measurement data to be deleted can be, for example, that which is stored in the memory 14. The dialog field 20 presents the user with two options for reacting to the posed question of whether the measurement data is to be deleted. These two options are represented by two text fields 22, 24, one of which contains the textual content "OK" and the other of which contains the textual content "Cancel". By means of the text field 22 ("OK") the user can confirm the intended deletion operation; by means of the text field 24 ("Cancel") he or she can, however, prevent the deletion operation. Each of the two text fields 22, 24 constitutes a second graphic element within the meaning of the invention; together they form or are at least part of a destination graphic arrangement. The textual contents "OK" and "Cancel" are chosen here by way of example. Various other textual and/or pictorial contents (e.g., "Yes"/"No") of equivalent meaning are alternatively conceivable.

The dialog field 20 contains a further graphic element which is arranged approximately midway between the two text fields 22, 24 and is formed as a sliding box 26 with a double-headed arrow 28 drawn therein. The sliding box 26 with the double-headed arrow 28 constitutes a first graphic element within the meaning of the invention. In its position shown in FIG. 1 midway between the two text fields 22, 24, the sliding box 26 marks a touching starting location, at which the user is to place his or her finger (or another pointing object) on the touchscreen 18, in order to drag from there the sliding box 26 either in the direction towards the text field 22 (for confirmation of the desired data deletion) or in the direction towards the text field 24 (for cancellation of the data deletion).

Deletion of data is in some cases an irreversible operation, which is why it is desirable to avoid unintended deletions. It is therefore not sufficient in the first embodiment according to FIGS. 1 and 2 to slide the sliding box 26 in the direction towards the text field 22 ("OK") and over this text field 22, as shown in FIG. 2. In this embodiment, the user must in addition keep his or her pointing object (represented in FIG. 2 by a finger 30) on the sliding box 26 for a specific minimum duration after he or she has slid the sliding box 26 over the text field 22. This minimum duration can be, for example, 0.5 or 1.0 or 1.5 or 2.0 seconds. The operating procedure for confirming the data deletion is thus composed of a first movement, in which the finger 30 is moved starting from the touching starting location up to the text field 22 (in this movement the sliding box 26 is displaced with the moving finger), a subsequent movement stoppage when the finger 30 has reached the region of the second text field 22, and, following that, a dwelling of the finger 30 in the region of the text field 22 for the preset minimum duration. Only when this operating pattern has been recognised by the control device 12 does the latter conclude that there is a successful input of a deletion command and accordingly deletes the desired data. A corresponding operating pattern (with a dwelling on the destination graphic element) may be necessary for the cancellation of the data deletion, i.e. when the sliding box 26 is moved in the direction towards the text field 24. Since the cancellation of the data deletion does not have irreversible consequences, however, a mere sliding of the sliding box 26 over the text field 24 without subsequent dwelling of the finger 30 may suffice for the cancellation of the data deletion.

Unintentional data deletion by an accidental swiping gesture in the direction towards the text field 22 is prevented by the procedure described above. The required stationary dwelling of the finger at the place of text field 22, after the sliding box 26 has been slid over the text field 22, constitutes a reliable hurdle against unintentional, accidental data deletions.

The movement path of the first movement is illustrated in FIG. 2 at 32; the beginning of the movement path lies at 34 and represents the movement starting location.

In the further figures, like or functionally similar elements are denoted by the same reference symbols as in FIGS. 1 and 2, but supplemented by a small letter. Unless otherwise stated below, reference is made to the above statements in connection with FIGS. 1 and 2 for the explanation of these elements.

Figure 3:
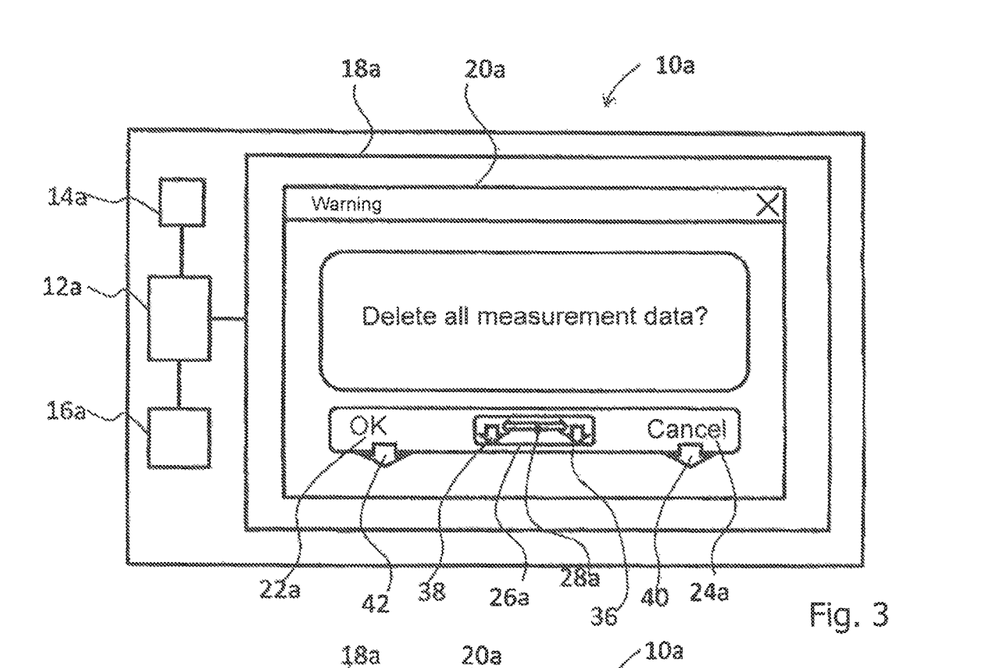
FIGS. 3 and 4 show a second embodiment for inputting an operating command in an ophthalmological apparatus via a touchscreen.
Figure 4:
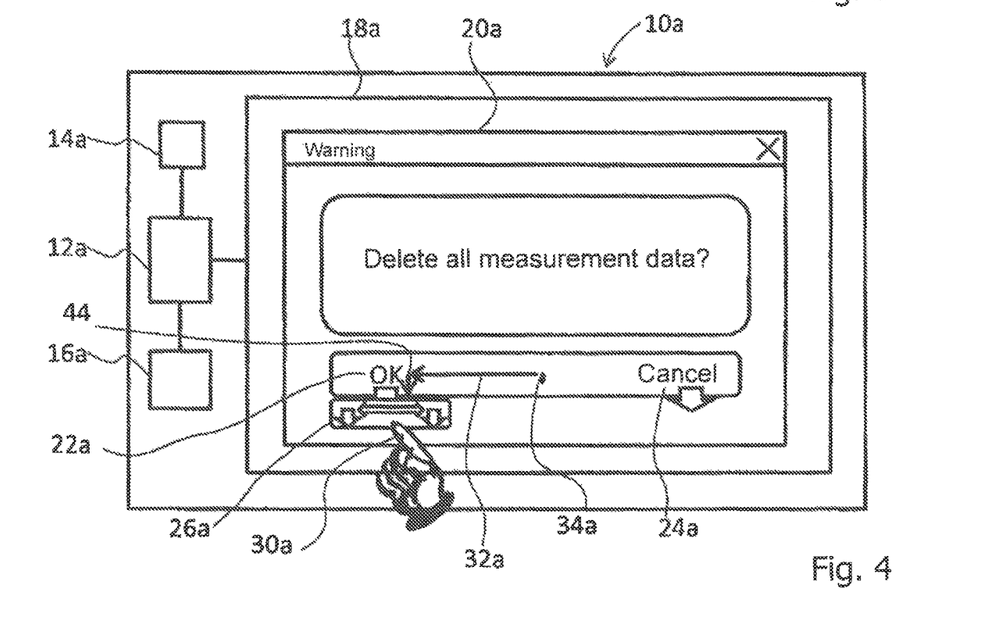

A partial region, shown in FIGS. 3 and 4, of an ophthalmological apparatus 10*a* according to the second embodiment has in a sliding box 26*a* of a dialog field 20*a*, apart from a double-headed arrow 28*a*, two further arrows 36, 38. Furthermore, two further arrows 40, 42 are also displayed adjacent to two text fields 22*a*, 24*a*. The further arrows 36, 38, 40, 42 are oriented in FIGS. 3 and 4 substantially parallel to one another and perpendicularly to the double-headed arrow 28*a*. Other movement paths, such as, for example, of a horizontal, oblique, circular or angular kind, will also be apparent to a person skilled in the art.

Furthermore, the ophthalmological apparatus 10*a* has all the features of the ophthalmological apparatus 10.

As in the first procedure described above, in a second procedure, described below, for inputting an operating command via the touchscreen 18*a* there is displayed a dialog field 20*a* with the question, by way of example, of whether existing measurement data is to be deleted. Unlike in the ophthalmological apparatus 10, however, in the ophthalmological apparatus 10*a* there is provided an operating pattern in which an object, for example, a finger 30*a*, for confirmation, instead of dwelling on the respective text field, has to perform a follow-up movement in the form of a hooked movement. In order to confirm the data deletion, the user in this embodiment thus has to drag the sliding box 26*a* from the touching starting location (beginning of the movement path 32*a*) at 34*a* to the text field 22*a* (first movement) and then deliberately move it on, in the direction of the arrow 42 arranged on the text field 22*a*, away from the text field 22*a* (transversely with respect to the direction of the first movement). This follow-up movement may, for example, have to take place over a predetermined distance, which is marked by the reference symbol 44 in FIG. 4. In particular, it is sufficient for the distance to correspond just to the detection resolution of the touchscreen, i.e. be just of such a length that a movement of the object in the direction of the arrow 42 is detectable by the touchscreen. Alternatively, it may be necessary for the distance to correspond at least to the length of the sliding box 26*a* in the longitudinal direction of the arrow 42. As the aforementioned dwelling, the moving-on here also constitutes a follow-up action within the meaning of the invention.

Between the first movement and the follow-up movement, a movement stoppage has to take place, i.e. it is necessary for the finger 30*a* to come to a standstill. Alternatively, however, it is also conceivable for the finger 30*a* not to stop completely, but reduce its absolute velocity or its velocity magnitude in the direction of the first movement by at least 50%. In this case, flowing movements for the command input are also suitable. Preferably, the finger 30*a* touches the touchscreen here during the entire command input, i.e. during the first movement, the movement stoppage and the follow-up movement, continuously. Alternatively, it is also conceivable for the finger, for confirmation of the command input, to be removed from the touchscreen after the first movement and the first movement repeated once starting from the touching starting point up to the text field 22*a* ("double swiping gesture") or for the second text field 22*a* for confirmation to be tapped after lifting off the finger 30*a* from the touchscreen.

In the second embodiment too, for the cancellation of the data deletion, an analogous operating pattern with a moving-on of the sliding box 26*a* after reaching the text field 24*a* may be required or a mere sliding of the sliding box 26*a* to the text field 24*a* may suffice. It is, moreover, conceivable for the arrows 38 and 42 to be oriented antiparallel or at any desired angle to the arrows 36, 40, with the result that the action to be performed for the confirmation can be differentiated more clearly from the action to be performed for the rejection. Additionally, a dwelling, described above in connection with the ophthalmological apparatus 10, may have to take place before or after the moving-on.

Figure 5:
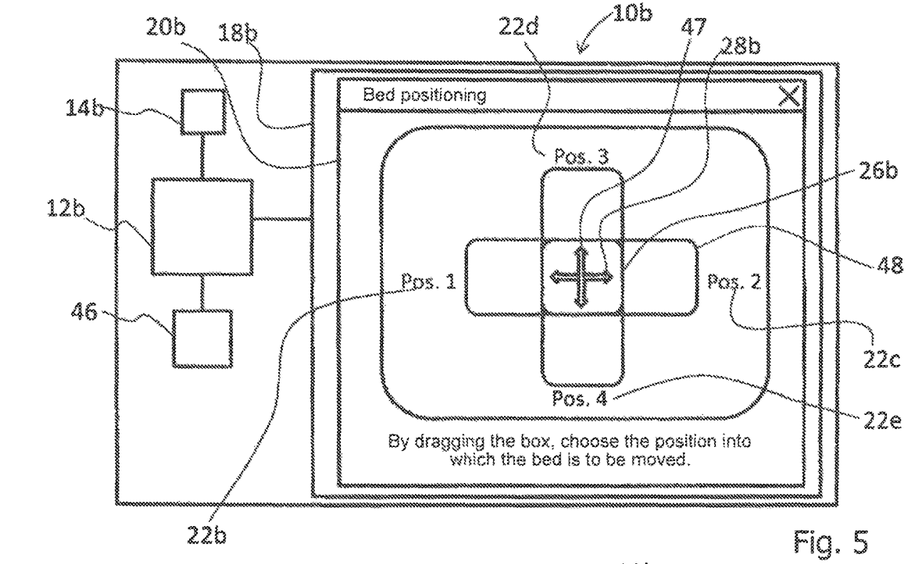
FIGS. 5 and 6 show a third embodiment for inputting a command for positioning a patient bed in an ophthalmological apparatus via a touchscreen.
Figure 6:
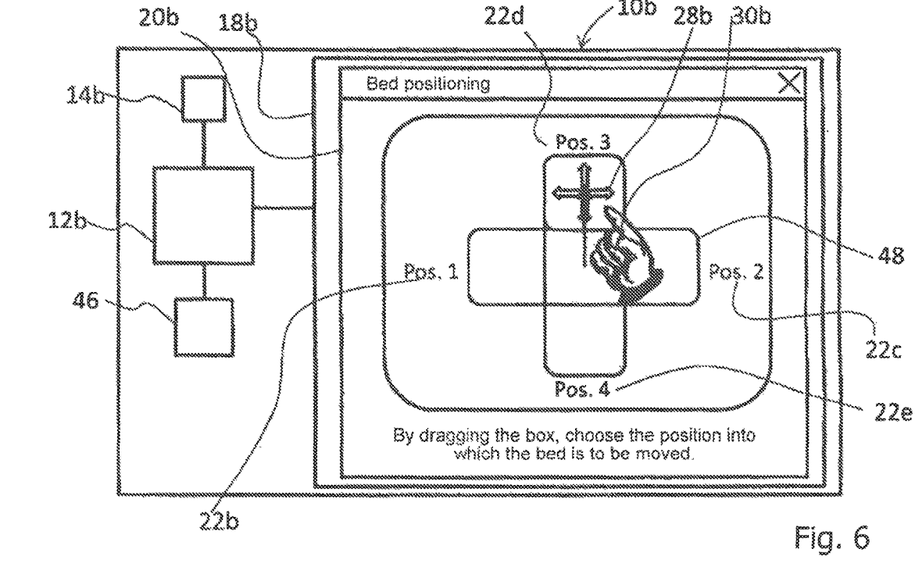

FIGS. 5 and 6 show an ophthalmological apparatus 10*b* according to a third embodiment which allows the user to adjust a position of a patient couch 46 in a manner free from errors. The patient couch 46 is electrically adjustable, i.e. positionable. For this purpose, it comprises at least one servomotor (not shown in the figures) which can be controlled by means of a control device 12*b*. The control device 12*b* is coupled to the patient couch 46, a memory 14*b* and a touchscreen 18*b*. To adjust the patient couch 46, the control device 12*b* retrieves characteristic position data from the memory 14 for the positioning of the patient couch and determines, for example, on the basis of a difference between an initial position of the patient couch and a position to which it is to be moved, control signals to be output to the servomotor. Since a person skilled in the art is familiar with the structure and functioning of patient couches, a detailed description is therefore dispensed with here. Instead of or in addition to the patient couch 46, the ophthalmological apparatus 10*b* can allow the user to adjust a patient chair, a slit lamp or a laser head in the same way.

In the third procedure, shown in FIGS. 5 and 6, for inputting an operating command via a touchscreen 18*b*, the patient couch 46 can be moved into four positions. In order to display to the user how such an operating command is to be input, there is displayed in a sliding box 26*b*, perpendicularly to a double-headed arrow 28*b*, a further double-headed arrow 47. Furthermore, at each of four mutually opposite ends of two intersecting strips, there is displayed in each case a text field 22*b*, 22*c*, 22*d*, 22*e* representing a position.

For the command input, provision is made, analogously to the first two embodiments, for the user to place his or her finger 30*b* on a touching starting location marked by the sliding box 26*b* and move it, while touching the screen 18*b*, in the longitudinal direction of one of the double-headed arrows 28*b*, 47, the sliding box 26*b* following the movement. In the case shown in FIG. 6, the user moves his or her finger here in such a manner upwards in the longitudinal direction of the double-headed arrow 47 that the sliding box 26*b* reaches one end of one of the strips at the text field 22*d*, in order to initiate a movement of the patient couch into the third position. For the confirmation of the command input, it is, moreover, necessary here for the control device 12*b* to recognise the operating pattern described in connection with the ophthalmological apparatus 10, in particular the dwelling of the finger 30*b* adjacent to the respective text field. Alternatively, however, the recognition of the operating pattern with the follow-up movement described in connection with the ophthalmological apparatus 10*a* may also be necessary. In this case, preferably additional arrows oriented perpendicularly to the double-headed arrows 28b, 47, as described above, would be displayed at the ends of the double-headed arrows 28b, 47.

The movement of the finger here may in particular have to take place until the end of the respective strip is reached while touching the touchscreen within a region 48 which is formed by the two intersecting strips and bordered by a line. In other words, a command input is considered to be cancelled when the finger leaves the bordered region 48 during the command input, before the end of the strip has been reached. While the sliding box 26b follows the finger 30b as long as the finger 30b touches the touchscreen 18 within the bordered region 48, the sliding box 26b returns to its original position at the touching starting location as soon as the finger leaves the region 48. The user is thereby informed that the command input has been cancelled. The sliding box here always moves as a whole within the bordered region 48 along one of the double-headed arrows 28b, 47.

Figure 7:
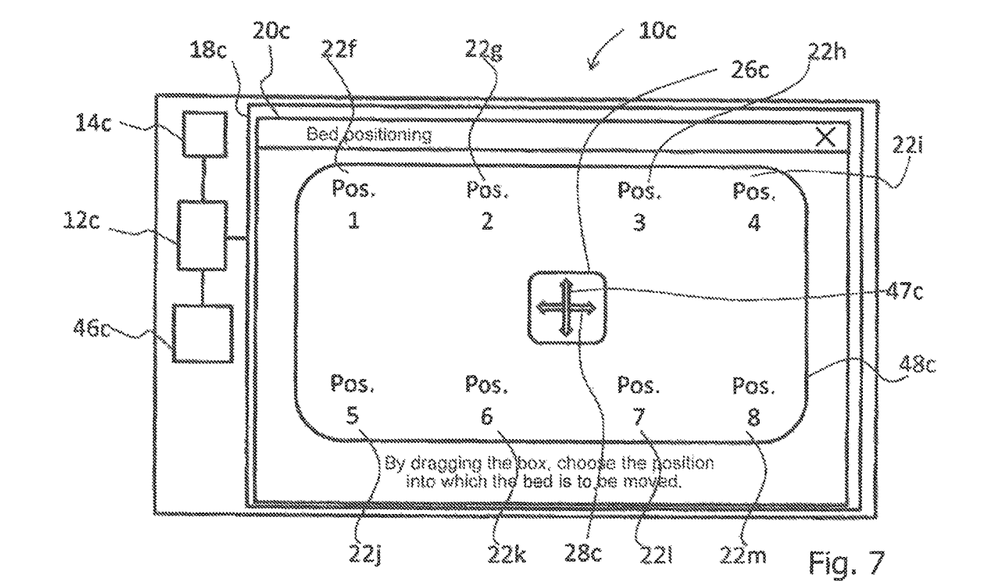
FIGS. 7 and 8 show a fourth embodiment for inputting a command for positioning a patient bed in an ophthalmological apparatus via a touchscreen.
Figure 8:
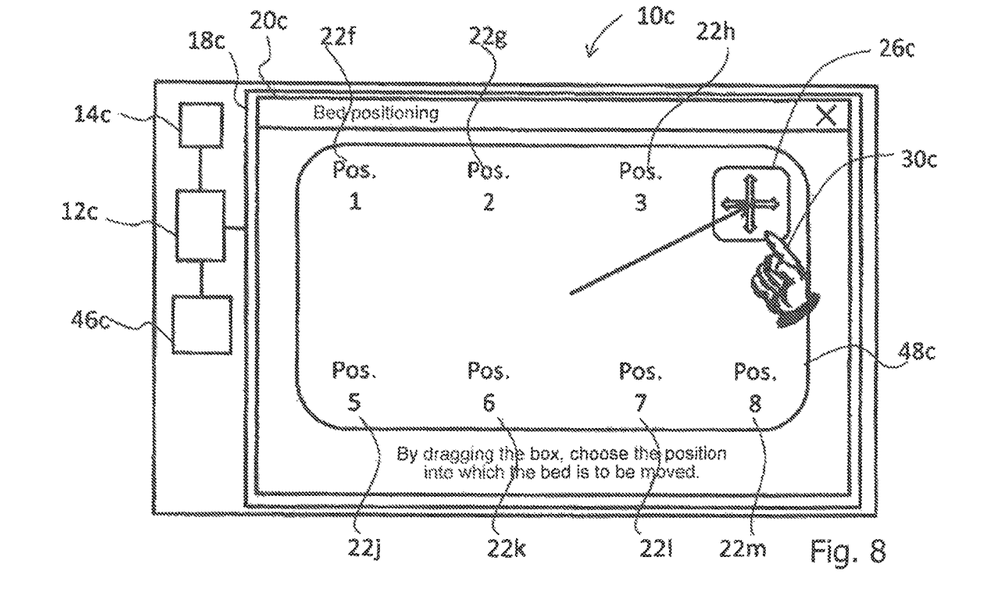

Unlike in the ophthalmological apparatus 10b, in an ophthalmological apparatus 10c according to a fourth embodiment provision is made for the user to be able to choose between eight instead of four positions of a patient couch 46c. The positions of the patient couch represent adjustment states. The ophthalmological apparatus 10c furthermore differs from the ophthalmological apparatus in that the sliding box 26c displayed on the touchscreen 18c is movable not only along one of the double-headed arrows 28c, 47c, but freely in the display plane of the touchscreen within a bordered region 48c. Moreover, the text fields 22f, 22g, 22h, 22i, 22j, 22k, 22l, 22m representing the eight positions are arranged within the bordered region 48c. As in the ophthalmological apparatus 10b, an operating command is considered to be cancelled as soon as a finger 30c does not touch the touchscreen 18c within the bordered region 48c, thus for example leaves the bordered region 48c during the first movement starting from the touching starting point up to one of the text fields. Alternatively, it may also be provided here that the first movement has to take place substantially linearly, i.e. de facto must follow a line connecting the touching starting location to the respective text field.

Furthermore, the ophthalmological apparatus 10c can have all other features of the ophthalmological apparatus 10b and be operated analogously.

Figure 9:
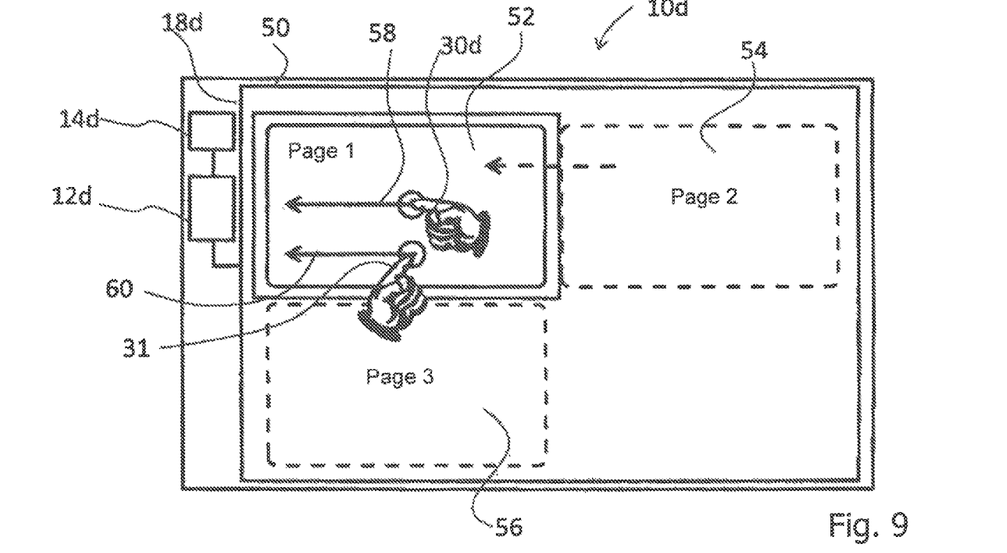
FIGS. 9 and 10 show a fifth embodiment for inputting a command for changing a page of an operating menu displayed on a touchscreen in an ophthalmological apparatus.
Figure 10:
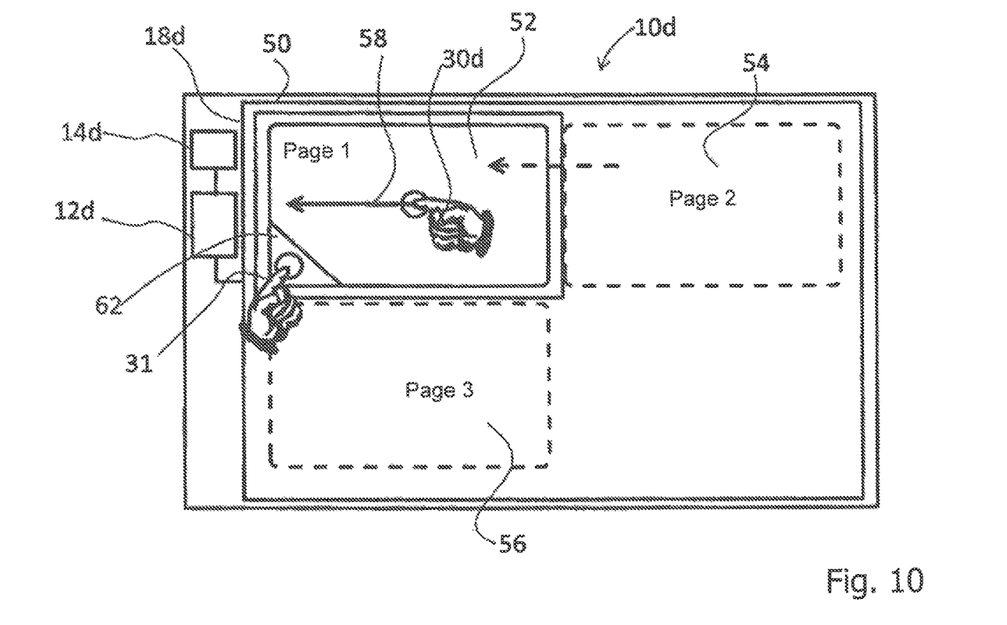

An ophthalmological apparatus 10d according to a fifth embodiment shown in FIGS. 9 and 10 comprises an electronic, program-controlled control device 12d which is connected to a memory 14d and a touchscreen 18d. Optionally, the control device 12d can additionally be coupled to a measuring device or a patient couch as in the embodiments described above. In the memory 14d there are stored, inter alia, a plurality of menu pages which may comprise, for example, textual and/or pictorial information, control buttons for executing applications and/or any desired input interfaces, and are to be displayed, for example, individually on the touchscreen. The control device 12d also determines here, from touch signals delivered by the touchscreen 18d, whether specific touch patterns are present which are to be interpreted as valid input of an operating command. Unlike in the first four embodiments, however, the operating command here is directed at switching between two menu pages, i.e. at changing the display of the touchscreen.

A first such menu page 52 is displayed on a touchscreen 18d in a program window 50. Furthermore, two second menu pages 54, 56 not displayed on the touchscreen 18d are represented in FIGS. 9 and 10 schematically bordered with broken lines and marked with the text "Page 2" and "Page 3", respectively.

FIGS. 9 and 10 represent two procedures alternative to one another for switching from the first menu page 52 to the second menu page 54. In the first procedure, shown in FIG. 9, for inputting an operating command for switching via the touchscreen, the user has to touch the touchscreen 18d with in each case one finger 30d, 31 of both hands within the program window in the region of the first menu page 52. Subsequently, the user has to draw the fingers 30d, 31 together, while touching the touchscreen 18d, in a direction away from the second menu page 54. The fingers are moved here together substantially parallel to one another in each case along a movement path 58, 60. The movements of the fingers 30d, 31 thus run longitudinally beside one another. In this embodiment, the movements are swiping movements. Alternatively, for example, dragging movements or equivalent types and forms of movement are conceivable. Neither the movement paths 58, 60 themselves, nor straight lines comprising the movement paths 58, 60, therefore intersect. For valid inputting of a movement command, it is necessary here for the movement paths 58, 60, i.e. the paths along which the fingers swipe over the touchscreen, to run substantially straight (linearly).

In the second procedure, illustrated in FIG. 10, the user has to move only the finger 30d; the finger 31 touches the touchscreen substantially stationarily in the left bottom corner region 62 of the program window 50. In this case, the control device 12d thus recognises the input of the operating command only when one of the fingers is moved, while the other rests stationary on the touchscreen in the corner region 62.

In ophthalmological treatments, it is necessary and desirable to finish the treatment in the shortest possible time, in order to keep the inconvenience for the patient to a minimum. The speed thereby required, however, promotes the occurrence of careless operating errors. With the procedures shown in FIGS. 9 and 10 for switching between the menu pages, inadvertent operating errors of the ophthalmological apparatus are effectively avoided. This is of great importance particularly in the case of the ophthalmological apparatuses, since operating errors there can quickly lead to irreparable damage to a patient's eye.

Although FIGS. 9 and 10 only show a movement pattern with which an operating command for switching between the first menu page 52 and the second menu page 54 is to be input, it is possible in the ophthalmological apparatus 10d to switch between the first menu page 52 and the second menu page 56 by means of an analogous movement pattern when, namely, the finger movement follows movement paths which are oriented perpendicularly to the movement paths 58, 60. The movement of the finger or the fingers 30d, 31 will then run vertically. Preferably, a movement coupling between the first 52 and each of the second menu pages 54, 56 causes a movement, at the same time and of the same kind as the movement of the first menu page 52, of the respective second menu page 54, 56.

The invention claimed is:

1. A method for controlling an apparatus equipped with a touchscreen, the method comprising:
   displaying, simultaneously on the touchscreen, a first graphic element and a destination graphic arrangement at a distance from the first graphic element, the first graphic element marking a touching starting location, at which a user is to place at least one object to start a first movement, the destination graphic arrangement including a plurality of second graphic elements arranged at a distance from one another, the plurality of second graphic elements comprising a confirmation graphic element signifying a confirmation of a called apparatus function, and a rejection graphic element signifying a rejection of the called apparatus function;

implementing the called apparatus function if the following occurs:

detecting the first movement of the at least one object over the touchscreen starting from the touching starting location continuously to the confirmation graphic element of the destination graphic arrangement;

detecting that the first movement results in the at least one object reaching the confirmation graphic element and a movement stoppage of the at least one object, the movement stoppage having a preset minimum duration;

detecting a follow-up action of the at least one object on the touchscreen, wherein the follow-up action comprises a follow-up movement of the object over the touchscreen starting from the confirmation graphic element reached in a transverse direction with respect to the first movement away from the confirmation graphic element; and in response to the first movement, the movement stoppage, and the follow-up action, executing an operating command associated with the called apparatus function;

cancelling the called apparatus function if the following occurs:

detecting a second movement of the at least one object over the touchscreen starting from the touching starting location continuously to the rejection graphic element, the second movement distinct from the first movement in not requiring any movement stoppage;

in response to only the second movement, absent any movement stoppage, cancelling the operating command associated with the called apparatus function.

2. The method according to claim 1, wherein the operating command is executed when the follow-up action is detected without intermediate lifting-off of the object from the touchscreen after the first movement.

3. The method according to claim 1, wherein the follow-up action further comprises a renewed movement of the object over the touchscreen starting from the touching starting location continuously up to the confirmation graphic element reached on the first movement.

4. The method according to claim 1, wherein the follow-up action further comprises a renewed touching by means of the object of the confirmation graphic element reached after intermediate lifting-off of the object from the touchscreen.

5. The method according to claim 1, wherein there is displayed on the touchscreen an optical indication which disappears depending on the follow-up action being performed.

6. The method according to claim 5, wherein the optical indication comprises a flashing of the first graphic element or of the confirmation graphic element reached on the first movement.

7. The method according to claim 1, wherein, on detection of the first movement, the first graphic element is displaced on the touchscreen in the direction towards the confirmation graphic element substantially synchronously with the moving object.

8. The method according to claim 7, wherein the displaced first graphic element is locked at the confirmation graphic element, in at least partial superimposition of the latter, depending on the follow-up action also being detected.

9. The method according to claim 7, wherein the displaced first graphic element is moved back after lifting-off of the object from the touchscreen as long as the follow-up action has not yet begun or is not yet concluded.

10. The method according to claim 1, wherein the called apparatus function is a function for storing or deleting or modifying data.

11. The method according to claim 1, wherein the operating command causes an adjustment of an adjustable component of the apparatus into one of a plurality of different predefined adjustment states, wherein each of these adjustment states is assigned a different second graphic element.

12. The method according to claim 1, wherein a haptic and/or visual and/or acoustic acknowledgement is output by the apparatus after at least part of the follow-up action.

13. An apparatus comprising:

a touchscreen; and a control device, coupled to the touchscreen, for executing an operating command which is input on the user side via the touchscreen, wherein the control device is adapted to:

simultaneously display on the touchscreen, a first graphic element and a destination graphic arrangement at a distance from the first graphic element, the destination graphic arrangement including a plurality of second graphic elements arranged at a distance from one another, the plurality of second graphic elements comprising a confirmation graphic element signifying a confirmation of a called apparatus function, and a rejection graphic element signifying a rejection of the called apparatus function;

implement the called apparatus function if the following occurs:

detect a first movement of at least one object over the touchscreen starting from a touching starting location at the first graphic element continuously up to the confirmation graphic element of the destination graphic arrangement and on reaching the confirmation graphic element and a movement stoppage of the object, the movement stoppage having a preset minimum duration;

detect a follow-up action of the at least one object on the touchscreen, the follow-up action comprises a follow-up movement of the object over the touchscreen starting from the confirmation graphic element reached in a transverse direction away from the confirmation graphic element; and execute an operating command associated with the called apparatus function in response to the first movement, the movement stoppage, and the follow-up action; and cancel the called apparatus function if the following occurs:

detect a second movement of the at least one object over the touchscreen starting from the touching starting location continuously to the rejection graphic element, the second movement distinct from the first movement in not requiring any movement stoppage;

in response to only the second movement, absent any movement stoppage, cancel the operating command associated with the called apparatus function.

14. The apparatus according to claim 13, wherein the operating instruction is executed upon detecting the follow-up action without intermediate lifting-off of the object from the touchscreen after the first movement.

15. The apparatus according to claim 13, wherein the follow-up action further comprises a renewed movement of the object over the touchscreen starting from the touching starting location continuously up to the confirmation graphic element reached on the first movement.

16. The apparatus according to claim 13, wherein the follow-up action further comprises a renewed touching by means of the object of the confirmation graphic element reached after intermediate lifting-off of the object from the touchscreen.

17. The apparatus according to claim 13, wherein the control device is adapted to cause the display on the touchscreen of an optical indication which disappears depending on the follow-up action being performed.

18. The apparatus according to claim 17, wherein the control device is adapted to output the optical indication as a flashing of the first graphic element or of the confirmation graphic element reached on the first movement.

19. The apparatus according to claim 13, wherein the control device is adapted to control the touchscreen in such a manner that, on detection of the first movement, the first graphic element is displaced on the touchscreen in the direction towards the confirmation graphic element substantially synchronously with the moving object.

20. The apparatus according to claim 19, wherein the control device is adapted to control the touchscreen in such a manner that the displaced first graphic element is locked at the confirmation graphic element, in at least partial superimposition of the latter, depending on the follow-up action also being detected.

21. The apparatus according to claim 19, wherein the control device is adapted to control the touchscreen in such a manner that the displaced first graphic element is moved back after lifting off the object from the touchscreen as long as the follow-up action has not yet begun or not yet ended.

22. The apparatus according to claim 13, the called apparatus function is a function for storing or deleting or modifying data.

23. The apparatus according to claim 13, wherein the control device is adapted, on recognising the command input, to adjust an adjustable component of the apparatus into one of a plurality of different predefined adjustment states, wherein each of these adjustment states is assigned a different second graphic element.

24. The apparatus according to claim 13, wherein the control device is adapted to cause the output of a haptic and/or visual and/or acoustic acknowledgement after at least part of the follow-up action.

25. The apparatus according to claim 13, wherein the control device is adapted to control the touchscreen in such a manner that, in response to a predefined operating command, a view on the touchscreen changes from a first menu page to a second menu page,
wherein the control device is adapted to recognise an input of the operating command depending on a first movement of the at least one object over the touchscreen being detected and simultaneously or at least partly temporally overlapping with respect thereto at least one further movement of:
a second object over the touchscreen along a movement path which is different from the movement path of the first movement being detected; or
a stationary dwelling of a third object on the touchscreen at a place distant from the movement path of the first movement being detected.

26. The apparatus according to claim 25, wherein the control device is adapted to recognise the input of the operating command depending on the first movement of the object over the touchscreen being detected and simultaneously or at least partly temporally overlapping with respect thereto at least one further movement of the object over the touchscreen along the movement path which is different from the movement path of the first movement being detected, and further depending on the movement paths of the first and each further movement running without intersecting one another.

27. The apparatus according to claim 26, wherein the control device is adapted to recognise the input of the operating command depending on the movement paths of the first and each further movement running longitudinally beside one other.

28. The apparatus according to claim 25, wherein the control device is adapted to recognise the input of the operating command depending on the first movement of the object over the touchscreen being detected and simultaneously or at least partly temporally overlapping with respect thereto the stationary dwelling of the third object on the touchscreen at the place distant from the movement path of the first movement being detected, and further depending on the stationary dwelling of the third object at a place within a predefined region of the touchscreen being detected.

29. The apparatus according to claim 28, wherein the predefined region is a corner region of the touchscreen.

\* \* \* \* \*